US009125655B2

(12) United States Patent
Gharib et al.

(10) Patent No.: US 9,125,655 B2
(45) Date of Patent: Sep. 8, 2015

(54) CORRECTION AND OPTIMIZATION OF WAVE REFLECTION IN BLOOD VESSELS (75) Inventors: Morteza Gharib, Altadena, CA (US); Niema Pahlevan, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 13/185,377

(22) Filed: Jul. 18, 2011

(65) Prior Publication Data

US 2012/0053672 A1 Mar. 1, 2012

Related U.S. Application Data (60) Provisional application No. 61/364,981, filed on Jul. 16, 2010.

(51) Int. Cl.
| *A61N 1/362* | (2006.01) |
| *A61F 2/06* | (2013.01) |
| *A61B 17/12* | (2006.01) |
| *A61B 5/02* | (2006.01) |
| *A61B 17/00* | (2006.01) |
| *A61B 19/00* | (2006.01) |

(52) U.S. Cl.
CPC .......... *A61B 17/12013* (2013.01); *A61B 5/02* (2013.01); *A61B 2017/00022* (2013.01); *A61B 2019/464* (2013.01); *A61N 1/362* (2013.01)

(58) Field of Classification Search
CPC .............. A61B 2019/464; A61B 5/02; A61B 17/12013; A61B 2017/00022; A61N 1/362
USPC .................... 600/16; 606/182, 191, 192, 194; 623/1.23, 1.3
See application file for complete search history.

(56) References Cited

U.S. PATENT DOCUMENTS

| 2,434,835 A | 1/1948 | Colley |
| 2,663,467 A | 12/1953 | Douglass et al. |
| 2,961,213 A | 11/1960 | Philippovic |
| 3,066,853 A | 12/1962 | Landenberger |
| 3,371,906 A | 3/1968 | Lubold |
| 3,504,550 A | 4/1970 | Koch et al. |
| 3,511,583 A | 5/1970 | Brown |
| 3,593,718 A | 7/1971 | Krasner et al. |
| 3,602,105 A | 8/1971 | Slusher |
| 3,638,536 A | 2/1972 | Kleinwachter et al. |
| 3,677,667 A | 7/1972 | Morrison |

(Continued)

FOREIGN PATENT DOCUMENTS

| WO | WO 92/06738 | 4/1992 |
| WO | WO 02/28450 A2 | 4/2002 |
| WO | WO 2005/011502 A2 | 12/2005 |

OTHER PUBLICATIONS

PCT/US2005/018455 ISR, Apr. 26, 2006.

(Continued)

*Primary Examiner* — Carl H Layno
*Assistant Examiner* — Erin Piateski
(74) *Attorney, Agent, or Firm* — ONE LLP (57) ABSTRACT The present invention provides methods and modalities that can modify wave reflection in the vascular system in order to create constructive interactions between existing wave dynamics and new reflective waves for the purpose of lowering the workload on the heart and increasing cardiac output, providing a viable option for the prevention and treatment of many heart conditions and diseases.

5 Claims, 7 Drawing Sheets

(56) References Cited

U.S. PATENT DOCUMENTS

| | | | |
|---|---|---|---|
| 3,730,186 A * | 5/1973 | Edmunds et al. | 606/158 |
| 3,756,243 A | 9/1973 | Schulte | |
| 3,768,931 A | 10/1973 | Willis, Jr. | |
| 3,982,722 A | 9/1976 | Bernard | |
| 4,092,010 A | 5/1978 | Carlson, Jr. | |
| 4,240,434 A | 12/1980 | Newkirk | |
| 4,256,094 A * | 3/1981 | Kapp et al. | 601/152 |
| 4,292,969 A | 10/1981 | Raible et al. | |
| 4,401,107 A | 8/1983 | Haber et al. | |
| 4,463,502 A | 8/1984 | Fitzgerald et al. | |
| 4,553,271 A | 11/1985 | Baker | |
| 4,602,911 A * | 7/1986 | Ahmadi et al. | 623/2.37 |
| 4,697,989 A | 10/1987 | Perlov et al. | |
| 4,705,518 A | 11/1987 | Baker et al. | |
| 4,721,030 A | 1/1988 | Paynter | |
| 4,794,912 A | 1/1989 | Lia | |
| 4,808,079 A | 2/1989 | Crowley et al. | |
| 4,915,017 A | 4/1990 | Perlov | |
| 4,917,579 A | 4/1990 | Torma | |
| 5,019,121 A | 5/1991 | Krauter | |
| 5,033,270 A | 7/1991 | Hardt | |
| 5,166,563 A | 11/1992 | Bassine | |
| 5,197,984 A | 3/1993 | Kedem | |
| 5,203,172 A | 4/1993 | Simpson et al. | |
| 5,344,385 A | 9/1994 | Buck et al. | |
| 5,394,132 A | 2/1995 | Poil | |
| 5,443,504 A | 8/1995 | Hill | |
| 5,549,619 A * | 8/1996 | Peters et al. | 606/151 |
| 5,562,595 A | 10/1996 | Neisz | |
| 5,637,083 A | 6/1997 | Bertrand et al. | |
| 5,653,676 A | 8/1997 | Buck et al. | |
| 5,678,564 A | 10/1997 | Lawrence et al. | |
| 5,697,884 A | 12/1997 | Franischelli et al. | |
| 5,697,952 A | 12/1997 | Franischelli et al. | |
| 5,701,919 A | 12/1997 | Buck et al. | |
| 5,716,379 A | 2/1998 | Bourgeois et al. | |
| 5,800,528 A | 9/1998 | Lederman et al. | |
| 5,984,857 A | 11/1999 | Buck et al. | |
| 5,996,964 A | 12/1999 | Ben-Shalom | |
| 6,030,334 A * | 2/2000 | Cox et al. | 600/12 |
| 6,053,210 A | 4/2000 | Chapman et al. | |
| 6,074,179 A | 6/2000 | Jokela et al. | |
| 6,076,013 A | 6/2000 | Brennan et al. | |
| 6,146,114 A | 11/2000 | Nardacci et al. | |
| 6,151,525 A | 11/2000 | Soykan et al. | |
| 6,224,540 B1 | 5/2001 | Lederman et al. | |
| 6,254,355 B1 | 7/2001 | Gharib | |
| 6,270,053 B1 | 8/2001 | Eshel | |
| 6,278,847 B1 | 8/2001 | Gharib et al. | |
| 6,314,322 B1 | 11/2001 | Rosenberg | |
| 6,331,188 B1 | 12/2001 | Lau et al. | |
| 6,343,605 B1 | 2/2002 | Lafontaine | |
| 6,352,553 B1 | 3/2002 | Van der Burg et al. | |
| 6,352,561 B1 | 3/2002 | Leopold et al. | |
| 6,361,637 B2 | 3/2002 | Martin et al. | |
| 6,395,016 B1 | 5/2002 | Oron et al. | |
| 6,408,878 B2 | 6/2002 | Unger et al. | |
| 6,428,464 B1 | 8/2002 | Bolling | |
| 6,450,942 B1 | 9/2002 | Lapanshvili et al. | |
| 6,464,476 B2 | 10/2002 | Ross et al. | |
| 6,506,025 B1 | 1/2003 | Gharib | |
| 6,508,756 B1 | 1/2003 | Kung et al. | |
| 6,517,570 B1 | 2/2003 | Lau et al. | |
| 6,520,986 B2 | 2/2003 | Martin et al. | |
| 6,551,350 B1 | 4/2003 | Thornton et al. | |
| 6,580,503 B2 | 6/2003 | Gharib et al. | |
| 6,582,208 B2 | 6/2003 | Gharib | |
| 6,607,368 B1 | 8/2003 | Ross et al. | |
| 6,608,668 B2 | 8/2003 | Gharib et al. | |
| 6,613,072 B2 | 9/2003 | Lau et al. | |
| 6,620,095 B2 | 9/2003 | Taheri | |
| 6,654,102 B1 | 11/2003 | Modares et al. | |
| 6,670,699 B2 | 12/2003 | Mikubo et al. | |
| 6,671,558 B1 | 12/2003 | Soykan et al. | |
| 6,672,847 B2 | 1/2004 | Dooley | |
| 6,679,687 B2 | 1/2004 | Gharib | |
| 6,713,944 B2 | 3/2004 | Omata et al. | |
| 6,716,002 B2 | 4/2004 | Higashino | |
| 6,717,172 B2 | 4/2004 | Gharib et al. | |
| 6,720,710 B1 | 4/2004 | Wenzel et al. | |
| 6,787,972 B2 | 9/2004 | Kim et al. | |
| 6,866,842 B1 | 3/2005 | Chancellor et al. | |
| 6,884,040 B2 | 4/2005 | Dooley | |
| 6,902,545 B2 | 6/2005 | Bertolero et al. | |
| 6,910,466 B2 | 6/2005 | Veinotte | |
| 6,956,230 B1 | 10/2005 | Gharib et al. | |
| 6,984,201 B2 | 1/2006 | Khaghani et al. | |
| 7,006,132 B2 | 2/2006 | Pereira et al. | |
| 7,021,604 B1 | 4/2006 | Werner et al. | |
| 7,031,775 B2 | 4/2006 | Soykan et al. | |
| 7,033,132 B2 | 4/2006 | Gharib | |
| 7,048,519 B2 | 5/2006 | Fong et al. | |
| 7,051,738 B2 | 5/2006 | Oron et al. | |
| 7,094,040 B2 | 8/2006 | Higashino et al. | |
| 7,104,313 B2 | 9/2006 | Pokharna et al. | |
| 7,107,777 B2 | 9/2006 | Vaiyapuri et al. | |
| 7,118,525 B2 | 10/2006 | Coleman et al. | |
| 7,155,288 B2 | 12/2006 | Soykan et al. | |
| 7,163,385 B2 | 1/2007 | Gharib et al. | |
| 7,331,991 B2 | 2/2008 | Kheradvar et al. | |
| 7,387,500 B2 | 6/2008 | Gharib | |
| 7,398,818 B2 | 7/2008 | Gharib et al. | |
| 7,491,170 B2 | 2/2009 | Gharib | |
| 7,524,298 B2 | 4/2009 | Gharib et al. | |
| 7,612,869 B2 | 11/2009 | Pereira et al. | |
| 7,749,152 B2 | 7/2010 | Gharib et al. | |
| 2003/0121644 A1 | 7/2003 | Tonosaki et al. | |
| 2003/0152469 A1 | 8/2003 | Dante et al. | |
| 2003/0164231 A1 | 9/2003 | Goodson et al. | |
| 2003/0209006 A1 | 11/2003 | Gharib et al. | |
| 2003/0233143 A1 | 12/2003 | Gharib et al. | |
| 2003/0234595 A1 | 12/2003 | Takahashi et al. | |
| 2003/0235504 A1 | 12/2003 | Lemoff et al. | |
| 2004/0013536 A1 | 1/2004 | Hower et al. | |
| 2004/0018100 A1 | 1/2004 | Takagi et al. | |
| 2004/0031594 A1 | 2/2004 | Vaiyapuri et al. | |
| 2004/0037035 A1 | 2/2004 | Ohashi et al. | |
| 2004/0048778 A1 | 3/2004 | Druggan | |
| 2004/0133260 A1 * | 7/2004 | Schwartz et al. | 623/1.1 |
| 2004/0143319 A1 * | 7/2004 | Schwartz et al. | 623/1.24 |
| 2004/0151607 A1 | 8/2004 | Gharib | |
| 2004/0152945 A1 | 8/2004 | Kantrowitz et al. | |
| 2004/0171904 A1 | 9/2004 | French et al. | |
| 2004/0184237 A1 | 9/2004 | Chang | |
| 2005/0008509 A1 | 1/2005 | Chang | |
| 2005/0070755 A1 * | 3/2005 | Zheng et al. | 600/16 |
| 2005/0092944 A1 | 5/2005 | Patterson | |
| 2005/0098299 A1 | 5/2005 | Goodson et al. | |
| 2005/0187620 A1 | 8/2005 | Pai et al. | |
| 2005/0197527 A1 | 9/2005 | Bolling | |
| 2005/0231914 A1 | 10/2005 | Mikubo et al. | |
| 2005/0265978 A1 | 12/2005 | Chancellor et al. | |
| 2005/0275494 A1 | 12/2005 | Gharib et al. | |
| 2005/0277865 A1 | 12/2005 | Gharib et al. | |
| 2006/0008450 A1 | 1/2006 | Verfaillie et al. | |
| 2006/0052866 A1 * | 3/2006 | Gilles et al. | 623/1.51 |
| 2006/0084835 A1 | 4/2006 | Laufer | |
| 2006/0106449 A1 * | 5/2006 | Ben Muvhar | 623/1.15 |
| 2006/0120048 A1 | 6/2006 | Houle et al. | |
| 2006/0131003 A1 | 6/2006 | Chang et al. | |
| 2006/0139882 A1 | 6/2006 | Mikubo et al. | |
| 2006/0147487 A1 * | 7/2006 | Henderson | 424/422 |
| 2006/0216173 A1 | 9/2006 | Kheradvar et al. | |
| 2006/0217588 A1 * | 9/2006 | Gross et al. | 600/16 |
| 2007/0185371 A1 | 8/2007 | Bortolotti | |
| 2008/0077070 A1 * | 3/2008 | Kopia | 604/8 |
| 2008/0097497 A1 * | 4/2008 | Assad et al. | 606/157 |
| 2008/0194905 A1 * | 8/2008 | Walsh | 600/17 |
| 2008/0260705 A1 | 10/2008 | Marban et al. | |
| 2009/0007923 A1 * | 1/2009 | Dancu | 128/898 |
| 2009/0088651 A1 | 4/2009 | Shuros et al. | 600/488 |
| 2009/0105631 A1 | 4/2009 | Kieval | |

(56) References Cited

U.S. PATENT DOCUMENTS

| | | | |
|---|---|---|---|
| 2009/0177270 A1* | 7/2009 | Agnew et al. | 623/1.24 |
| 2009/0281560 A1* | 11/2009 | Wexner et al. | 606/153 |
| 2010/0114299 A1* | 5/2010 | Ben Muvhar et al. | 623/1.24 |

OTHER PUBLICATIONS

PCT/US2005/018592 ISR, Dec. 6, 2006.
PCT/US2005/047234 ISR, Feb. 16, 2007.
PCT/US2006/000986 ISR, Sep. 5, 2007.
PCT/US2007/000309 ISR, Nov. 2, 2007.
PCT/US2008/008539 ISR, Jun. 16, 2009.
PCT/US2011/059597 ISR, Jun. 21, 2012.
PCT/US2005/018455 IPRP, Nov. 29, 2006.
PCT/US2005/018592 IPRP, Dec. 2, 2006.
Avrahami, I., et al., "Computational studies of resonance wave pumping in compliant tubes", J. Fluid Mech., 2008, vol. 608, pp. 139-160.
Caro, C., et al., "The Mechanics of the Circulation", Cambridge University Press, $2^{nd}$ Edition, 2012, pp. 238-255.
Curtis, S.L., et al., "Reduced systolic wave generation and increased peripheral wave reflection in chronic heart failure", Am J Physiol Heart Circ Physiol, 2007, vol. 293, pp. H557-H562.
Helm, P., et al., "Measuring and Mapping Cardiac Fiber and Laminar Architecture Using Diffusion Tensor MR Imaging", Ann. NY Acad. Sci., 2005, vol. 1047, No. 1, pp. 296-307.
Hickerson, A.I., et al., "Experimental study of the behavior of a valveless impedance pump", Experiments in Fkuids, 2005, vol. 38, pp. 534-540.
Hickerson, A.I., et al., "On the resonance of a pliant tube as a mechanism for valveless pumping", J. Fluid Mech., 2006, vol. 555, pp. 141-148.
Kannel, W.B., et al., "Changing epidemiological features of cardiac failure", Br Heart J., 1994, vol. 72, No. 2, Supplement, S3-S9.
Lloyd-Jones, D.M., et al., "Lifetime risk for developing congestive heart failure: the Framingham Heart Study", Circulation, 2002, vol. 106, No. 24, pp. 3068-3072.
Mitchell, G.F., et al., "Pulsatile Hemodynamics in Congestive Heart Failure", Hypertension, 2001, vol. 38, pp. 1433-1439.
Mitchell, G.F., et al., "Arterial stiffness and cardiovascular events: the Framingham Heart Study", Circulation, 2010, vol. 121, No. 4, pp. 505-511.
Moser, M., et al., "Prevention of disease progression, left ventricular hypertrophy and congestive heart failure in hypertension treatment trials", J. Am. Coll. Cardiol., 1996, vol. 27, No. 5, pp. 1214-1218.
PCT/US2005/047234 IPRP, Jul. 3, 2007.
PCT/US2006/000986 IPRP, Sep. 25, 2007.
PCT/US2007/000309 IPRP, Jul. 8, 2008.
PCT/US2008/008539 IPRP, Jan. 12, 2010.
PCT/US2011/059597 IPRP, May 13, 2014.
Nichols, W.W., et al., "McDonald's Blood Flow in Arteries: Theoretical, Experimental and Clinical Principles, Sixth Edition", CRC Press, 2011, pp. 170-222.
Ooi, H., et al., "Arterial Stiffness and Vascular Load in Heart Failure", Congestive Heart Failure, 2008, vol. 14, No. 1, pp. 31-36.
Pahlevan, N.M., et al., "Aortic Wave Dynamics and Its Influence on Left Ventricular Workload", PLoS One, 2011, vol. 6, No. 8, pp. 1-8.

\* cited by examiner

CORRECTION AND OPTIMIZATION OF WAVE REFLECTION IN BLOOD VESSELS

CROSS-REFERENCE TO RELATED APPLICATIONS

This application claims priority to and the benefit of co-pending U.S. provisional patent application Ser. No. 61/364,981 filed Jul. 16, 2010, which application is incorporated herein by reference in its entirety.

FIELD OF INVENTION

The invention relates generally to methods and devices that can treat symptoms and conditions in the vascular system as well as the field of wave optimization technology.

BACKGROUND

Congestive heart failure (CHF) has reached an epidemic proportion in the U.S. and worldwide with serious consequences in terms of human suffering and economic impact. In the U.S. alone, there are 60,000 patients dying each year with CHF as the underlying cause. Approximately 5,800,000 Americans have been diagnosed with this condition and this number is increasing every year. In the absence of myocardial infarction, hypertension is a primary risk factor of CHF (D. Lloyd-Jones et al. (2002) *Circulation* 106: 3068-3072) mainly due to the chronic elevation of the left ventricular (LV) workload and the development of left ventricular hypertrophy (LVH) (W. Kannel et al. (1994) *British Heart Journal* 72: S3-S9; G. Mitchell et al. (2010) *Circulation* 121: 505-511; and M. Moser et al. (1996) *J Am Coll Cardiol* 27: 1214-1218).

Healthy heart function is based on a delicate balance between its pumping capacity (cardiac output, stroke volume) and the input resistance of the receiving vascular system. The pumping mechanism of the heart is pulsatile—with each heartbeat, the heart sends a wave of pressure surge accompanied by local vessel dilation throughout the vascular conduits. The intensity and pulsatility of this pressure and the dilation wave decreases as the waves enter smaller vessels and eventually disappear in the capillary bed. Therefore, wave dynamics dominates the hemodynamics of large vessels such as the ascending, descending and abdominal aorta.

In this respect, vascular resistance in large arteries is composed of a primary viscous component and a dynamic component that is a function of wave characteristics such as frequency (heart beat), amplitude (stroke volume), wave length, and pressure-flow phase difference which depends on the elastic and viscoelastic properties of the carrier vessel. In the electrical circuit terminology, the frequency-dependent component of vascular resistance is known as "impedance." Essentially, this dynamic resistance is the response of the vascular system as a compliant system to the pressure and wall expansion waves that originate at the root of the aorta during the systolic phase.

It is known (W. Nichols et al. (2005) "McDonald's Blood Flow in Arteries: Theoretical, Experimental and Clinical Principles") that pressure wave reflection from branching points (renal arteries etc.), or from sudden changes in the wall properties such as thickness, diameter or stiffness can grossly change the resistance that the heart experiences during the cardiac cycle. Stiffening of the aorta due to aging or vascular diseases, for instance, hampers the ability for blood vessels to vasodilate. This effect is a major source of elevated systemic resistance and thus blood pressure. Such stiffening also results in a change in the wave speed and length of forward propagating waves as well as the nature of their interaction with the reflective waves.

While efforts have been made trying to elucidate the role of wave reflections in heart failure (S. Curtis et al. (2007) *Am J Physiol Heart Circ Physiol* 293: H557-562; and G F Mitchell et al. (2001) *Hypertension* 38: 1433-1439), and clinical studies have confirmed that abnormal pulsatile loads play an important role in the pathogenesis of LVH and CHF (Supra G. Mitchell et al. (2010); H. Ooi et al. (2008) *Congestive Heart Failure* 14: 31-36), conventional cardiology in general ignores this wave dynamic and its impact on the vascular resistance mainly due to the complexity of the wave interaction process. Therefore, there is a need for novel methods and devices that take advantage of recently gained insights in hemodynamics in the treatment and prevention of heart diseases and heart failure.

SUMMARY OF THE INVENTION

While it is known in the art to use a ventricular assistance device (VAD) which includes an artificial pump to treat patients suffering from congestive heart failures, the inventors are not aware of any attempt at utilizing reflective waves to lessen the workload on the patient's heart.

Accordingly, the present invention provides methods and devices aimed at creating an artificial reflection wave in the vascular system for the purpose of reducing a cardiac load. In one aspect of the invention, a device implantable in a mammal is provided with a biocompatible material configured to generate an artificial pressure wave reflection site in a blood vessel in the mammal. The artificial pressure wave reflection site is configured to reduce a hemodynamic load on the mammal's heart as compared to a hemodynamic load exerted by the blood vessel without the artificial pressure wave reflection site. In an embodiment, the device is a band that can be configured to have curvature for constricting the blood vessel at the reflection site or otherwise applying pressure at the reflection site.

In one feature, the device of the invention is configured to be changed by an adjustment, such that at least one parameter selected from the group consisting of an activation state, an axial distance from an aortic input, an axial width, a diameter, a flexibility, a durometer and a shape. The adjustment may be effected by a control module that the device is in communication with. The control module may be configured to be set by at least one of actors selected from the following: a human operator, a microcomputer-based device having instructions recorded on a machine-readable medium, and a remote device in communication with the control module. The control module may be further in communication with a sensor configured to detect at least one physiological parameter related to blood flow, such as a heart rate, a pressure wave at an aortic input, a flow wave at an aortic input, an arrival time of incoming pressure wave in the blood vessel, an arrival time of incoming flow wave in the blood vessel, and a rigidity of the blood vessel.

In another embodiment, the device of the invention includes multiple reflection-changing elements that can be individually activated and deactivated. Embodiments of the reflection-changing element include a ring, a band, a graft, or a stent.

In another aspect of the invention, a kit is provided with the device described above as well as instruction on where to implant the implantable device in the mammal. In an embodiment, the kit further includes a control module configured to make adjustment to the device. Further, the kit may also include a sensor in communication with the control module and configured to detect at least one physiological parameter related to blood flow. The sensor and/or the control module can also be implantable. In one embodiment, the control module is in communication with a pacemaker.

In yet another aspect of the invention, a method of reducing a hemodynamic load on a mammal's heart is provided. The method includes the step of affecting a reflective wave in the mammal's blood circulation, e.g., in the aorta. In an embodiment, the method of the invention provides a new artificial pressure wave reflection site in a blood vessel in the mammal, e.g., in the abdominal aorta. In an embodiment, the new reflection site is proximate to the renal bifurcation In an alternate embodiment, the method of the invention adjusts the rigidity of the blood vessel.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification, including definitions, will control. In addition, the materials, methods, and examples are illustrative only and not intended to be limiting. All patents and publications cited in this specification are incorporated herein by reference in their entirety.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Definitions

Malleable: capable of being extended, shaped or bent by mild impact or pressure without losing its physical integrity, i.e., without breaking.

Biocompatible: suitable for exposure to the body or bodily fluids without causing chemical reactions known to be adverse to the organism.

In a series of in-depth in vitro experimental, theoretical and computational studies, Gharib and his students at California Institute of Technology have affirmatively shown that wave reflection can result in added positive or negative pumping effect in flow loops that consist of a compliant tube connected to well-defined reflective sites. In particular, studies done by Hickerson and Gharib (*J. Fluid Mech.* (2006) 555: 141-48) as well as by Avrahami and Gharib (*J. Fluid Mech.* (2008) 608: 139-60) have demonstrated that in tubes with dimensions similar to adult human aorta and with similar compliance properties, one can produce forward or retrograde flow by simply changing the frequency and duty cycle of pulsatile flows. Through these studies, it was shown that the observed pumping effects are due to the positive and negative interaction between incoming and reflective waves at the reflection sites.

The present invention is based on the recent discovery that the wave reflection process in parts of the vascular system, e.g., the aorta, can be manipulated (through constructive interaction with reflective waves) to produce a forward pumping effect and/or to correct an adverse pumping effect that may exist due to negative interactions between forward waves with reflective waves. These interactions are complex. In a healthy, young adult, the pressure wave originating from the heart can be traveling at the speed about 6 m/s in the aorta, making several rounds in the aorta and the rest of the arterial system in the duration of a single heartbeat. Therefore, before a cardiac pressure wave dies out, reflections stemming from it could encounter other waves in additive/constructive or interruptive/destructive manners due to phase differences. In the case of a constructive interaction, the reflective wave serves as a net forward flow (away from the heart). The pump (or the heart) receives added help from a compliant tube (the aorta) due to its ability to provide additional pumping in series with the main pump (heart), reducing the heart's overall loading. In the case of a destructive interaction, the reflective wave serves as a net retrograde flow (towards the heart). The pump (or the heart) is presented with additional resistance since the elastic tube (or aorta) now acts as an anti-pump against the pump's (or the heart's) output.

The present invention encompasses methods and modalities that can modify wave reflection in the vascular system in order to create constructive interactions between existing wave dynamics and reflective waves for the purpose of increasing net forward flow or reducing vascular impedance. This lowers the workload on the heart and increases cardiac output, providing a viable option for the prevention and treatment of many heart conditions and diseases, especially those associated with different types of heart failure such as congestive heart failure (CHF), acute heart failure (AHF), and systolic heart failure. For example, patients with hypertension (high blood pressure) of any type (essential hypertension, secondary hypertension, isolated systolic hypertension, or resistant hypertension) and left ventricular hypertrophy (LVH) who are in danger of suffering from heart failures can benefit from therapeutic embodiments of the present invention as reduction of pulsatile load through the present techniques can significantly improve left ventricular (LV) function in patients. In addition, the device of the invention can also be used as a medical assistance device for all of the above mentioned diseases as well as other cardiovascular diseases such as diastolic heart failure and ischemic heart disease.

According to the present invention, in order to reduce the workload on the heart, a reflective wave in the blood circulation, e.g., in the aorta, is provided. In one embodiment, this is achieved through modifying the physical property of an existing part or locus in the vascular system, e.g., the rigidity of a portion of the aortic wall (e.g., through the use of a band). In another embodiment, this is achieved through the introduction of a new, artificial reflection site. A single device or multiple devices can be used to on a single patient to practice the invention and these devices are individually and collectively termed "reflection-changing element" or "reflection-changing elements" for purposes of this disclosure.

Figure 1:
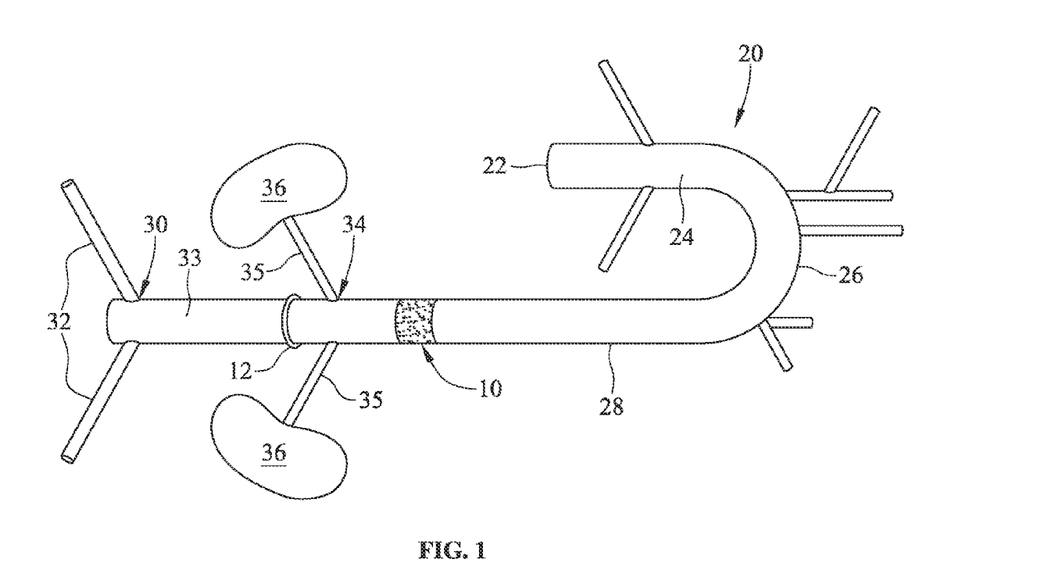
FIG. 1 is a side view of an aorta model with reflection-changing elements of the invention placed over parts of the aorta.

Referring to FIG. 1, the simplest form of the reflection-changing element is a band 10, which is a strip of material configured to have curvature for constricting part of the vasculature and can fully encircle or partially encircle around a blood vessel. The band can be made of any suitable material, and for implanting purposes, a biocompatible material, such as a metal, an alloy, a plastic, a fabric or a combination of any of the above. In some embodiments, the band 10 is made of one or more malleable materials such that an operator (e.g., a surgeon) can manually adjust its curvature to achieve the right amount of constriction over a selected vascular site. The band 10 can have a variety of configurations that vary in thickness, axial width and diameter. In some embodiments, the band 10 has an axial width between about 4 cm and about 8 cm. In one embodiment, the band 10 is a full-circle ring 12. The reflection-changing element of the invention is placed or implanted at a predetermined position to create a new reflection site or shift an existing reflection site from its natural position to a new position that is more favorable in terms of added wave pumping capability. The band 10 can be a strip of biocompatible fabric wrapped around that location in a constricting manner similar to a bandage. It can be immobilized through the use of an adhesive or other conventional attachment devices such as a suture. If the band 10 is a full circle ring 12, it can be an open ring that is closable after being delivered to the desired implanting location, e.g., in a mechanism similar to rings found in a three-ring binder. In one embodiment, the ring 12 is secured to the vessel wall by a strip of self-adhesive bandage wrapped around the ring.

FIG. 1 shows the reflection-changing element implanted over a tube designed to simulate an aorta 20, the largest artery in human and other mammals. The aorta originates from the left ventricle of the heart (not shown) at the point of aortic input or aortic root 22, and can be divided into a section called the ascending aorta 24, a section called the Arch of aorta 26, and a section called the descending aorta 28, which ends at the iliac bifurcation 30 where the aorta divides into the common iliac arteries 32. In the lower part of the descending aorta 28 called the abdominal aorta 33, there is also a renal bifurcation 34 where the aorta branches and extends, through renal arteries 35, into the kidneys 36. The reflection-changing element of the invention can be placed at or near any suitable site in the vasculature, preferably in close proximity to a major artery such as the aorta. In one embodiment, the reflection-changing element of the invention is implanted at the descending aorta, preferably the abdominal aorta. In a particular embodiment, the reflection-changing element of the invention is implanted between the renal bifurcation site 34 and the iliac bifurcation site 30 of the aorta, e.g., underneath or distal to the renal bifurcation site 34, e.g., ring 12 as shown in FIG. 1.

When multiple elements are used, the reflection-changing elements of the invention can be implanted at multiple locations in the vasculature at the same time or in sequence. At any given time in a patient, the reflection-changing elements can be of the same configuration or different. While the embodiments illustrated in FIG. 1 are placed outside a blood vessel, one skilled in the cardiovascular art should readily understand that they can be placed inside a blood vessel, for example, by use of delivery and deployment devices similar to those used with stents and other cardiovascular implants (e.g., a balloon catheter). For example, a collapsible ring, band, graft or stent can be placed over a balloon in a catheter and delivered via the femoral veins to a desired site before being expanded and immobilized against the artery wall as the balloon is inflated.

The reflection-changing elements illustrated in FIG. 1 may be passive in the sense that they are meant to be permanent or semi-permanent implants that, once implanted, would remain the same configuration in the same location for an extended period of time, possibly for life. Some of the materials suitable for making the passive embodiments include fabrics such as silk, polyester (e.g., sold under the trade name Dacron®), shape memory alloys and thermoplastic polymers such as polyethylene (PE) and polytetrafluoroethylene (PTFE). Moreover, there are also dynamic or interactive embodiments where a reflection-changing element of the invention is adjustable and adjusts according to a changing physiological condition of the patient.

Figure 2:
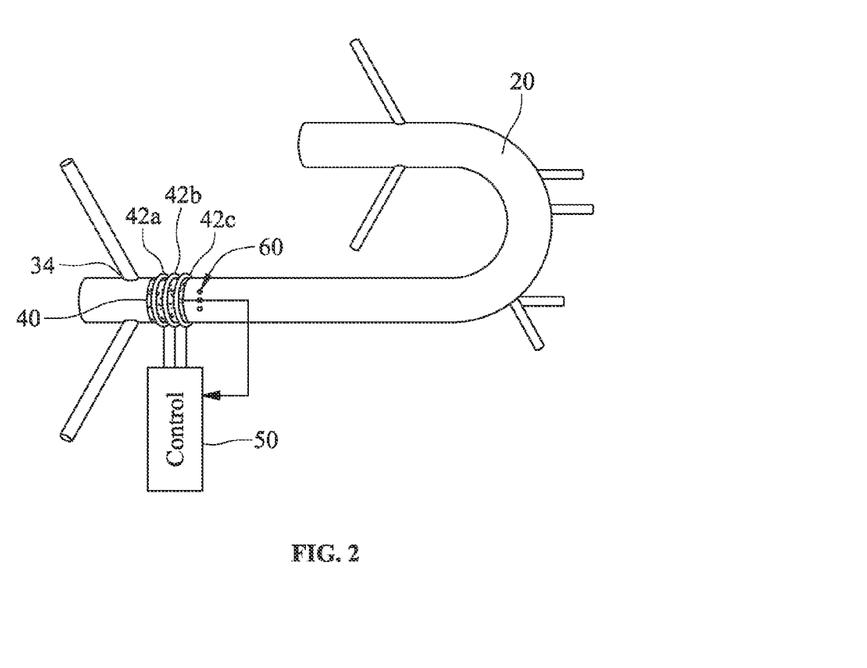
FIG. 2 is a side view of an aorta model with another embodiment of the reflection-changing element shown over the aorta.

Referring now to FIG. 2, a dynamic embodiment of the reflection-changing element of the invention is shown as a cuff 40 that can be wrapped around an aorta 20 at a strategic position (e.g., proximate to the renal bifurcation 34). The cuff 40 consists of one or multiple controllable, smaller bands that are susceptible to remote adjustment and control. Three such bands 42a, 42b and 42c are shown in the figure. Materials that can be used to makes these adjustable bands include and are not limited to active polymers, inflatable materials, ferromagnetic materials, and shape memory alloys. One or more adjustable bands can be implanted in a patient at a given time. Each of the adjustable bands 42a, 42b and 42c is in communication with a control module 50. In some embodiments, the control module 50 is remote (e.g., outside the patient body). In other embodiments, the control module 50 may be implanted within the body of the patient. In one embodiment, the control module 50 can effect changes in various parameters of the adjustable band, e.g., its activation state (on or off), axial distance of the artificial reflection site from the aortic input (location), axial width, diameter, flexibility, durometer and shape. As an example, one embodiment of the adjustable band can change in terms of flexibility such that it can be more or less stiff through the use of piezoelectric materials or a ferro-magnetic gel (or fluids) around the band.

The adjustment may be based on a control input with feedback from a sensor 60, shown here as fastened to the aorta wall next to the cuff 40, that changes the reflection site dynamically in order to promote constructive wave interaction. In some embodiments, the sensor 60 is a pressure sensor. In other embodiments, the sensor is a motion sensor. For example, the sensor 60 could be based on an interdigitated array of elements that provide a capacitive signal. In some embodiments, a dual array of interdigitated elements, having on array aligned to measure an axial signal, and a second array aligned to measure a longitudinal signal, can be used to obtain values for axial and longitudinal pressures or motions. In the case of having ferro-magnetic gel in the reflection-changing element, the sensor can be an electrical current sensor that sends out feedback signal based on transmural pressure changes and the control module in turn sends control signal to change the current in the gel and consequently change the stiffness or flexibility of the gel.

Figure 3:
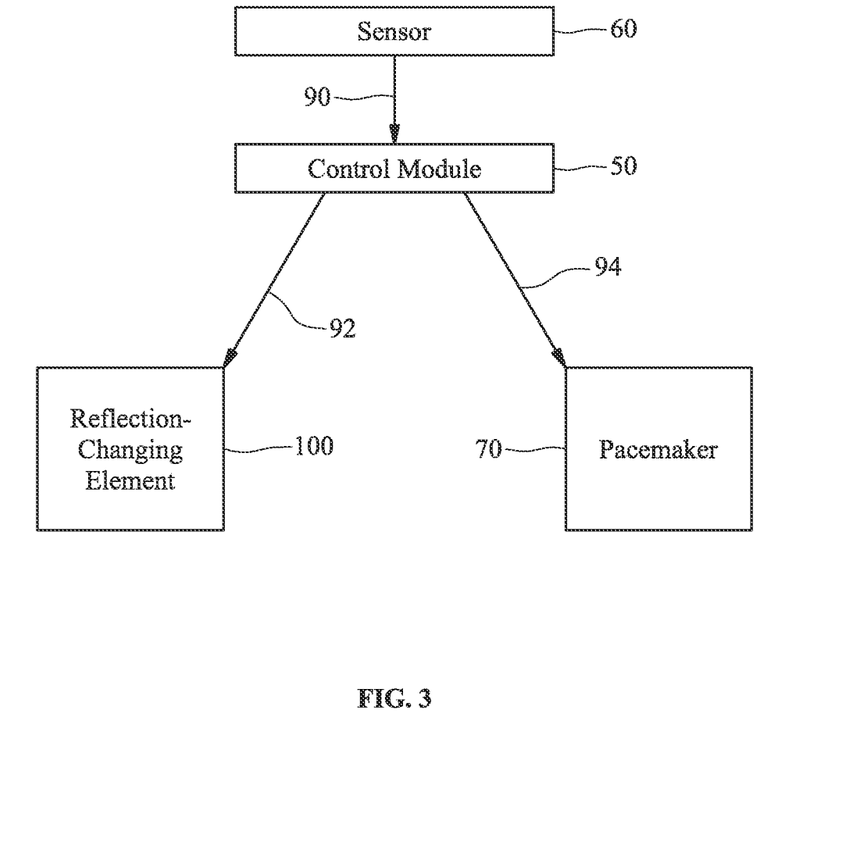
FIG. 3 is a flow chart showing the relations among components of a dynamic embodiment the invention when in operation.

The control module 50 can be set by at least one or more of the following: a human operator (e.g., a surgeon), a microcomputer-based device having instructions recorded on a machine-readable medium, and a remote device in communication with said control module 50. FIG. 3 illustrates how various components in a dynamic embodiment of the invention operate. One or more sensors 60 detect one or more physiological parameter related to blood flow, e.g., a heart rate, a pressure wave at an aortic input, a flow wave at an aortic input, an arrival time of incoming pressure wave in the blood vessel, an arrival time of incoming flow wave in the blood vessel, and a rigidity of the blood vessel. In step 90, sensor 60 sends the detected information to the control module 50, which processes the information and executes a command in step 92 for the reflection-changing element 100 to make an adjustment (e.g., to activate by changing from a relaxed state to a constricted state or vice-versa). The control module 50 may be further in communication with a third implant device that can affect one of the physiological parameters being detected by the sensor 60 such that the control module 50 can, via this third implant device, change the value of the parameter. For example, as described below, efficacy of the reflection-changing element 100 of the present invention may depend on the heart rate of the patient. Therefore, when the control module 50 also controls a pacemaker 70 through step 94, it can modify the heart rate such that the reflection-changing element of the invention could be better utilized to assist the patient in lessening the workload on the heart. The individual electrical connections between any two of sensor 60, control module 50, pacemaker 70 and reflection-changing element 100 can be wired or wireless. Wireless communication among all parts listed in FIG. 3 can be achieved, as one skilled in the art readily understands, by using currently available communication technologies and protocols such as those relying on radio waves and are not described in further detail here.

Figure 4:
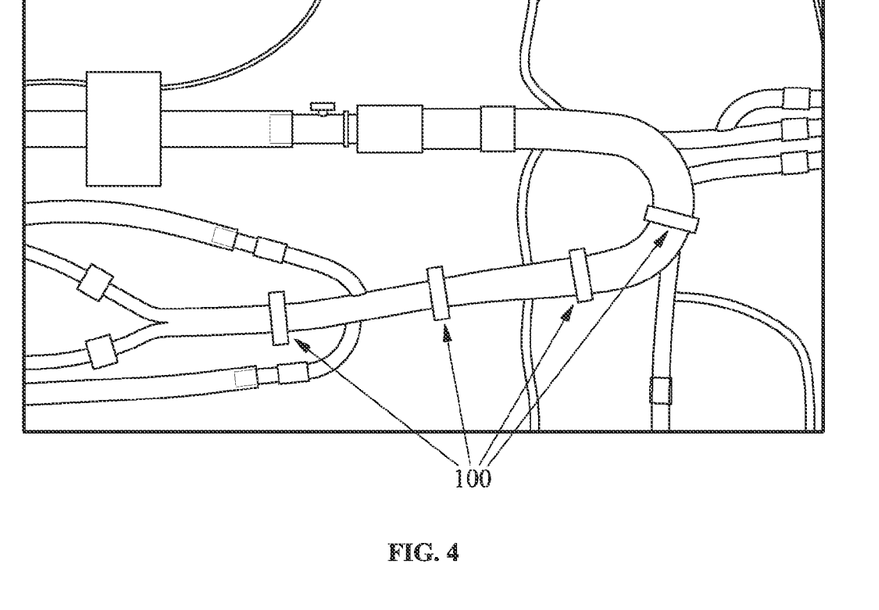
FIG. 4 shows an embodiment of the invention that includes multiple reflection-changing elements and their placement on an aorta model.

Referring now to FIG. 4, in one embodiment, the implantable device of the invention includes multiple reflection-changing elements 100 that can be individually activated and deactivated. In one exemplary method to practice the invention, an area of the vasculature, e.g., the entire aorta, is first identified in an adult male patient as the potential site for implanting the device of the invention. The patient's aorta is then determined to be about 52 cm long, e.g., through imaging techniques such as MRI. Four adjustable bands or rings, marked as 1-4, are selected to be implanted over the length of the aorta starting at about 15 cm from the aortic input and then with a space of about 10 cm in between each other as summarized in Table 1. All four bands are wirelessly connected to a control module (not shown). A sensor is implanted in proximity to the left ventricle, e.g., at the aortic input, to determine if workload on the left ventricle has been sufficiently lessened as the control module activates the adjustable band 1 first and the bands 2, 3, and 4 in sequence (always with the other three inactive). Alternatively, a network of sensors that measures blood pressure and flow over various parts of the aorta can be employed to calculate LV workload. Then the operator can decide which of the four bands should remain active based on feedback from the sensor. Alternately, a control module can be linked wirelessly to the sensor and can decide which band to activate (and which bands to deactivate) based on continued feedback from the sensor.

TABLE 1

| Item   | Distance from Aortic Root | Axial width  |
|--------|---------------------------|--------------|
| Band 1 | 15 cm                     | About 0.5 cm |
| Band 2 | 25 cm                     | About 0.5 cm |
| Band 3 | 35 cm                     | About 0.5 cm |
| Band 4 | 45 cm                     | About 0.5 cm |

Further embodiments of the invention include kit embodiments where various combinations of the reflection-changing elements, the control module, the sensor, the delivery devices, are included with appropriate instructions of use. In one embodiment, instruction on where to implant the reflection-changing elements is also include, e.g., directing the user to implant them in aortic locations such as the abdominal aorta.

EXAMPLES

Figure 5A:
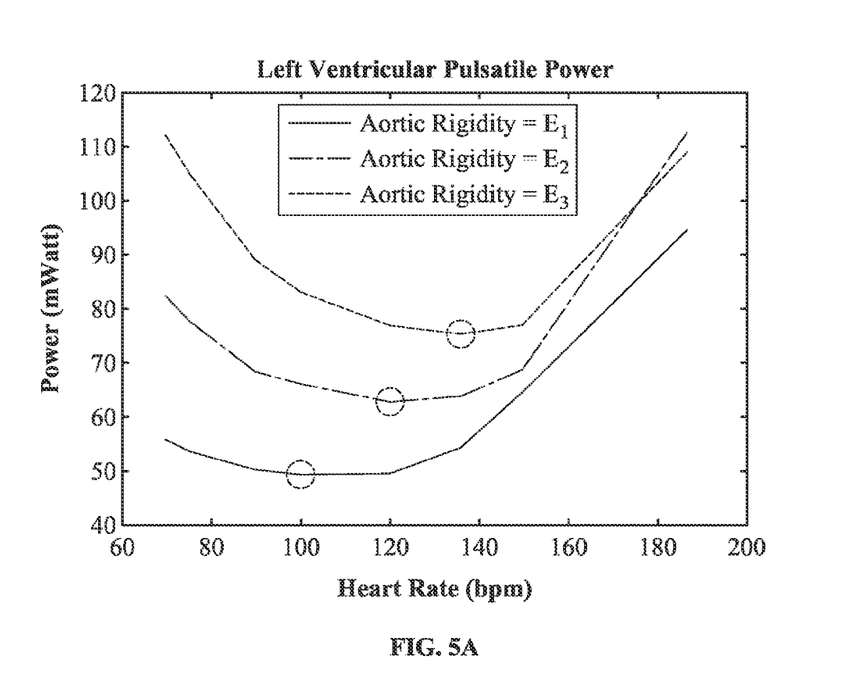
FIG. 5A and FIG. 5B are graphs illustrating the LV pulsatile power at different heart rates for an aorta model. Each plot line represents data collected for a given aortic rigidity.
Figure 5B:
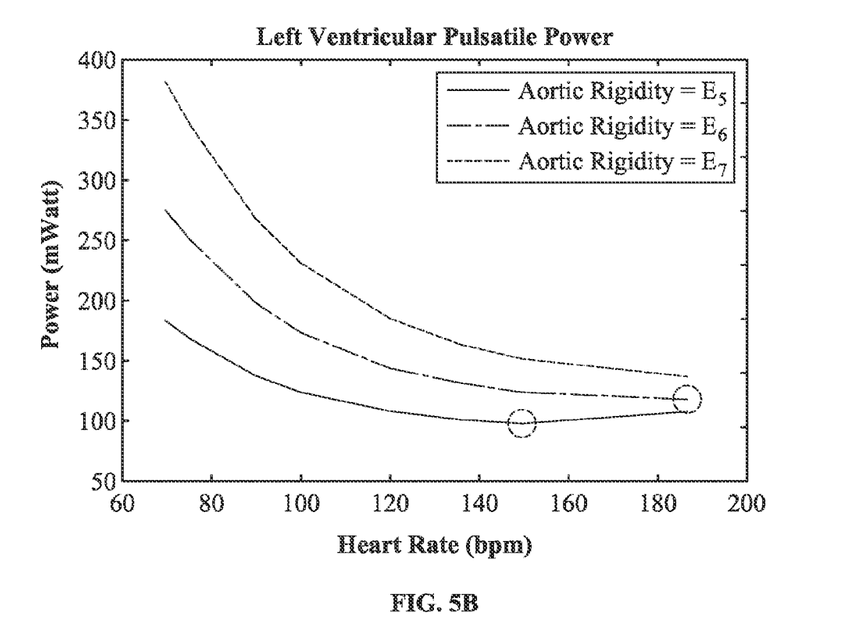

Aortic wave dynamics depend on heart rate, aortic compliance/wall rigidity, and the locations of reflection sites (Supra, I. Avrahami et al. (2008); and A. Hickerson et al. (2005) *Experiments in Fluids* 38: 534-540). The inventors have demonstrated, in "Aortic Wave Dynamics and Its Influence on Left Ventricular Workload" (2011, in press at PLos), that aortic waves have an optimum condition at which the left ventricular (LV) workload is minimized. FIGS. 5A and 5B show that at any given aortic rigidity, there exists an optimum heart rate (HR) that minimizes the LV power requirement for a set amount of cardiac output. For example, for aortic rigidity value $E_1$, the optimum HR is around 100. At that HR, the LV pulsatile power reaches a minimum value of around 50 mWatt in an three-dimensional axisymmetric aorta model based on physiological data from C. Caro et al. (1978, Oxford University Press) "The Mechanics of the Circulation." Since the total LV power consists of the pulsatile power and a steady power, the total workload on LV is minimized when the pulsatile load on LV reaches the minimum value. FIGS. 5A and 5B also show that the optimum HR shifts to higher values as the aorta becomes more rigid, i.e., goes from $E_1$ to $E_2$, $E_3$, $E_5$, $E_6$ and $E_7$, where $E_1 < E_2 < E_3 < E_5 < E_6 < E_7$.

Figure 6:
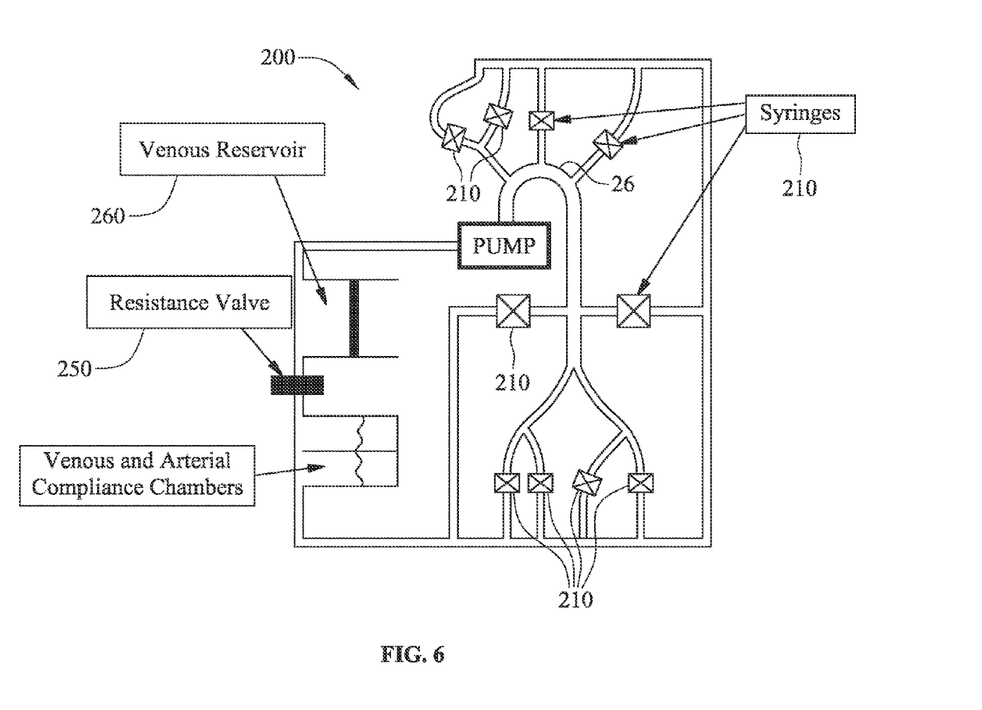
FIG. 6 is a schematic view of an aortic simulator used for collecting data presented in FIG. 9 to FIG. 11.

Referring now to FIG. 6, an aortic simulator 200 was used to study whether the reflection-changing elements of the invention can reduce the workload on a patient's LV. The simulator 200 was a hydraulic model with physical and dynamical properties similar to the human aorta and was used for in-vitro hemodynamic study of the mammalian, in particular, human vascular system. The model included aortic arc 26 and main branches of the aorta, and was built in a 1-1 scale of a typical human aorta. Geometrical parameters were within the range of published physiological data. Syringes 210 were provided at the end of each branch to simulate the compliance of omitted vascular bed. The syringe 210 was half filled with air to give the requisite compliance. The arterial resistance was control by using the syringe 210 at each branch and a resistance valve 250 at the end of the hydraulic circuit (before the reservoir 260).

In-vitro experiments were performed using the aortic simulator 200 illustrated in FIG. 6. The aortic simulator 200 was set up and run for an artificial compliant model of the aorta for various heart rates in the range {60, 72, 100, 120, 160} beats per minute (bpm). Cardiac output was fixed at 5 liters/min for all cases. The pressure and velocity (flow) data at the aortic input (aortic root) was collected to compute pulsatile ($\overline{P}_{pulse}$) and total left ventricular power ($\overline{P}_{total}$) using Equation 1 and 2 (shown below). No ring or band was used, and data was collected as control.

$$\overline{P}_{total} = \frac{1}{T} \int_0^T p(t)q(t) \quad (1)$$

$$\overline{P}_{pulse} = \overline{P}_{total} - \left(\frac{1}{T}\int_0^T p(t)dt\right)\left(\frac{1}{T}\int_0^T q(t)dt\right) \quad (2)$$

where p(t) is the pressure, q(t) is the flow, and T is the period of the cardiac cycle.

A. Ring

Figure 7:
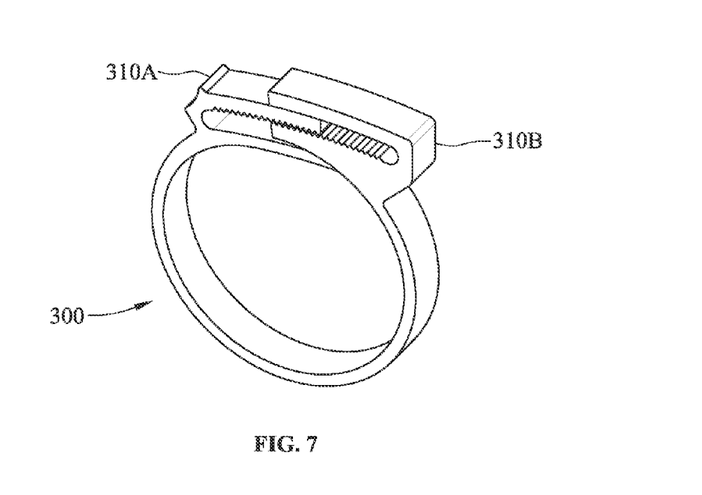
FIG. 7 is a perspective view of a ring used as an embodiment of the reflection-changing element.

Referring to FIG. 7, a ring 300 with a single snap grip, was used as an embodiment of the reflection-changing element of the invention. The ring 300 has two grip ends 310A and 310B, and by squeezing the two grip ends 310A and 310B, an operator can decrease the diameter of the ring 300 and lock in the diameter by virtue of the engaged teeth. This motion is reversible when the operator wishes to increase the ring 300's diameter. The ring 300 had an axial width of about 0.5 cm and was made of plastic. The ring was placed at a pre-selected site over the aorta simulator as shown in FIG. 4 (one ring at all times), and its inner diameter adjusted to be about 1 mm narrower than the tubular diameter at the site of placement. The four preselected sites correspond anatomically to the Aortic Arch, Thoracic Aorta, Upper Abdominal Aorta and Lower Abdominal Aorta from position 1 to 4, respectively (see Table 2 below for more detail).

B. Band

Figure 8:
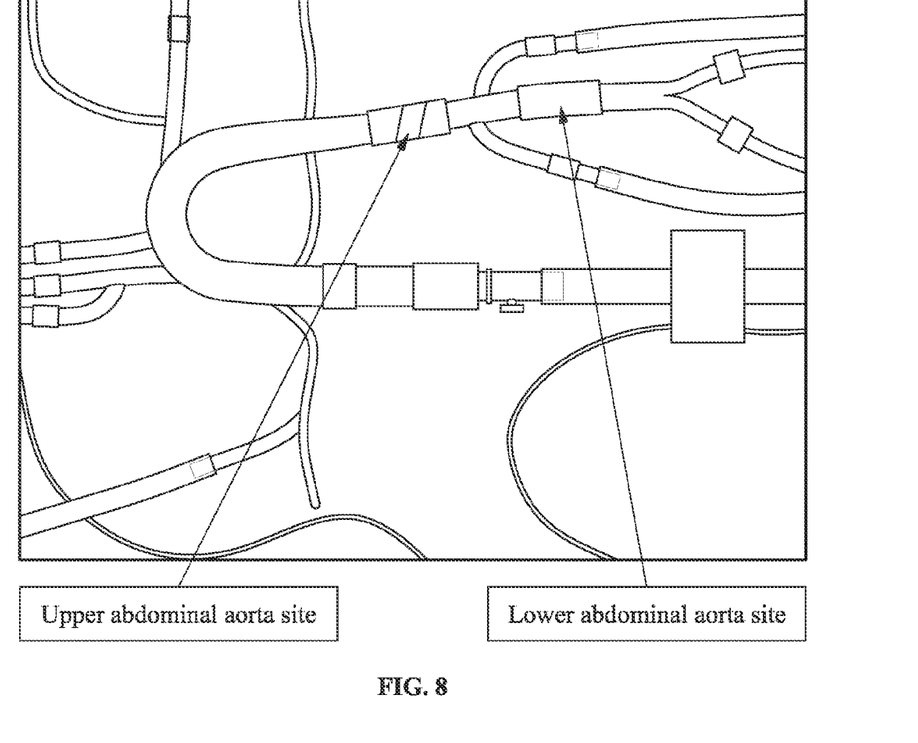
FIG. 8 shows two locations for a band as an embodiment of the reflection-changing element on the aortic simulator illustrated in FIG. 6.

Referring to FIG. 8, a band made of Polytetrafluoroethylene (PTFE) and about 7 cm wide was used as an embodiment of the reflection-changing element of the invention. The band was wrapped around the simulated aorta at one of two preselected sites on the aorta: upper abdominal aorta or lower abdominal aorta. As the band was significantly stiffer than the compliant tube of the aortic tube, it created an extra reflection site without significantly constricting the encircled aorta. Geometrical data of the ring and band are summarized in Table 2 below.

TABLE 2

| Item | Distance from Aortic Input (Aortic Root) | Axial width | Diameter |
|---|---|---|---|
| Ring 1 | 15 cm | About 0.5 cm | 28 mm |
| Ring 2 | 24-25 cm | About 0.5 cm | 27 mm |
| Ring 3 | 33-35 cm | About 0.5 cm | 23.5 mm |
| Ring 4 | 44-45 cm | About 0.5 cm | 21.5 mm |
| Upper abdominal band | 33 cm | 7 cm | n/a |
| Lower abdominal band | 45 cm | 7 cm | n/a |

Experiments were repeated with the same setup as the control, but with a ring or a band placed at different location along the aorta as depicted in FIG. 4 and FIG. 8, respectively, in order to create an artificial reflection site. The pulsatile LV power ($\overline{P}_{pulse}$) and the total LV power ($\overline{P}_{total}$) were calculated as described above. This artificial reflection site altered the wave dynamics in the simulated aorta, showing that it would be possible to control waves in such a way that the load on the heart can be reduced.

Figure 9:
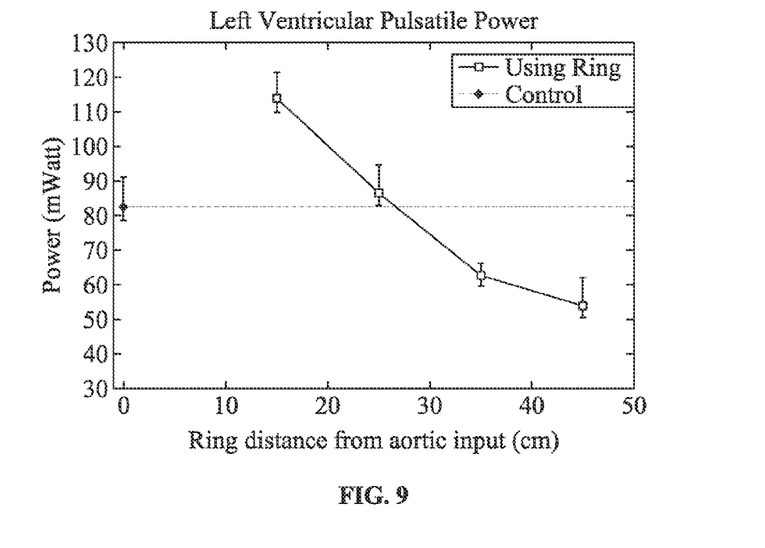
FIG. 9 charts the resulting LV pulsatile power as a ring is placed at different distance from the aortic root (heart rate at 60 bpm).
Figure 10:
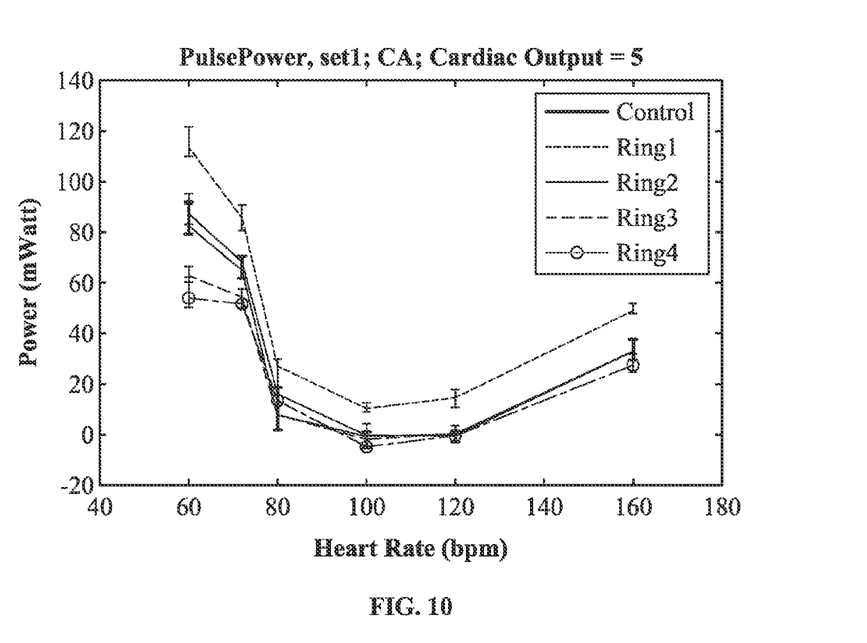
FIG. 10 charts the resulting pulsatile power at different heart rates for each ring location.

Results for the ring experiment are shown in FIG. 9 and FIG. 10. As illustrated in FIG. 9, LV pulsatile load can increase or decrease depending on the ring location. These specific data were collected at HR=60 bpm, and showed that in this particular embodiment and when HR is about 60 bpm, the ring implanted at both abdominal aorta locations (locations 3 and 4) significantly lowered the LV workload.

FIG. 10 shows the LV pulsatile power for the control case (no ring) versus having a ring at location 1 to 4 at different heart rates (HR). There was a clear advantage of using a ring at low HR (60 bpm) and medium low HR (72 bpm). At locations 3 and 4, the passive ring was shown to reduce the hemodynamic load on the heart for a range of heart rates, namely, between about 60 to about 80 bpm for the specific rigidity tested here, which approximately equals the aortic rigidity of a 45-50 year old healthy male person.

Figure 11:
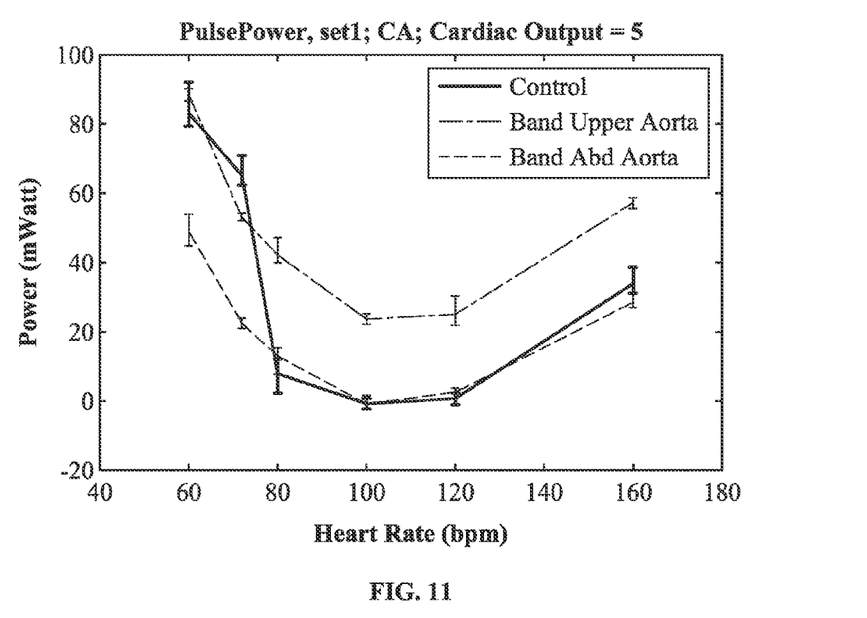
FIG. 11 charts the resulting pulsatile power at different heart rates for each band location.

FIG. 11 shows the pulsatile power for the control case versus two different band locations at different heart rates (HR). There is a clear advantage of using the band at the lower abdominal location at low-medium HRs (60 and 72). Similar to the ring, at the lower abdominal location, the passive band was shown to reduce the hemodynamic load on the heart for a range of heart rates, namely, between about 60 to about 80 bpm for the specific rigidity tested which approximately equals the aortic rigidity of a 45-50 year old healthy male.

For the aortic rigidity condition under which data for FIG. 9 to FIG. 11 were collected, the control system was at its optimum condition with a HR in the range of 100-120 bpm (pulsatile power reached zero), making it impossible for a reflection-changing element to make much difference close to the optimum HR of 100 bpm. However, as shown in FIG. 5A and FIG. 5B, as the arterial rigidity increases, the optimum HR also increases, going past 180 bpm, Therefore, as arterial rigidity increases, it becomes much broader for the range of heart rates over which the reflection-changing element of the invention can be used to reduce the cardiac workload. In various embodiments, that range of effective heart rates may be no less than 5, 10, 20, 30, 40, 50, 60, 70, 80, 90 or 100 bpm. Also, in various embodiments, the percentage of reduction in the LV load may be no less than 5, 10, 20, 30, 40, 50 or 60%.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material. In the event of a conflict, the conflict is to be resolved in favor of the present disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

We claim:

1. A system implantable in a mammal along the mammal's aorta, comprising:
   a plurality of inelastic members comprising biocompatible material, each member being a fully encircling ring that is set to have the same diameter throughout use in the same location once implanted,
   the members positioned around the aorta, each member having a curvature for constricting the aorta and spaced apart from one another to generate a plurality of artificial pressure wave reflection sites in the aorta to reduce a hemodynamic load on the mammal's heart as compared to a hemodynamic load without the artificial pressure wave reflection sites.

2. The device of claim 1, wherein at least one of the plurality of members consists of a unitary strip of fabric wrapped around the aorta and immobilized by an adhesive or a suture.

3. The device of claim 1, adapted to be changed by an adjustment, during implantation only.

4. The device of claim 3, adapted to be changed in at least one parameter for the plurality of members, the parameter selected from an axial distance from the aortic root and a diameter.

5. The device of claim 1, wherein each of the plurality of members consists of a unitary ring with engaged teeth for diameter adjustment and lock in, and each of the rings consists of plastic.

* * * * *